(12) United States Patent
Jäkel et al.

(10) Patent No.: US 7,816,107 B2
(45) Date of Patent: Oct. 19, 2010

(54) METHOD FOR PRODUCING AN OPTICALLY ACTIVE 2-METHYL-ALKANE-1-OL FROM THE CORRESPONDING 2-METHYLALK-2-EN-1-AL, COMPRISING CARBONYL-SELECTIVE REDUCTION, ENANTIOSELECTIVE HYDRATION AND LIPASE-CATALYZED, STEREOSELECTIVE ACYLATION IN ORDER TO ENRICH THE DESIRED

(75) Inventors: Christoph Jäkel, Limburgerhof (DE); Gunnar Heydrich, Limburgerhof (DE); Rainer Stürmer, Ródersheim-Gronau (DE); Rocco Paciello, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 444 days.

(21) Appl. No.: 11/576,317

(22) PCT Filed: Sep. 22, 2005

(86) PCT No.: PCT/EP2005/010240
§ 371 (c)(1),
(2), (4) Date: Mar. 29, 2007

(87) PCT Pub. No.: WO2006/034812
PCT Pub. Date: Apr. 6, 2006

(65) Prior Publication Data
US 2008/0108117 A1 May 8, 2008

(30) Foreign Application Priority Data
Sep. 29, 2004 (DE) .................. 10 2004 047 836

(51) Int. Cl.
*C12P 7/04* (2006.01)
(52) U.S. Cl. .................................. 435/157
(58) Field of Classification Search ............ 435/157
See application file for complete search history.

(56) References Cited
U.S. PATENT DOCUMENTS
5,288,928 A 2/1994 Broger et al.

FOREIGN PATENT DOCUMENTS
EP 0492401 7/1992
EP 0529698 A2 3/1993

OTHER PUBLICATIONS

Hogberg, et al. J. Org. Chem. 1992, 57, pp. 2052-2059.*
Bianchi, D. et al., "Anhydrides as acylating agents in lipase-catalyzed stereoselective esterification of racemic alcohols," J. Org. Chem., 1988, vol. 53, pp. 5531-5534.
Barth, S. et al., "Lipase-catalyzed resolution of racemic 2-alkyl substituted 1-alkanols[1]," Tetrahedron: Asymmetry, 1993, vol. 4, pp. 823-833.
Högberg, H. E., "Approaches to 2-methyl-1-alkanols of high enantiomeric purities via enzyme mediated reactions," Microbial Reagents in Organic Synthesis, 1992, vol. 381, pp. 399-410.
Jermyn, M. A., "An extension of the Halpern-Westley procedure for resolving alcohols," Aust. J. Chem., 1967, vol. 20, pp. 2283-2284.
Oppolzer, W. et al., "25. Camphorsulfonamide-shielded, asymmetric 1,4-additions and enolate alkylations; synthesis of a Southern Corn Rootworm pheromone," Helvetica Chimica Acta, 1985, vol. 68, pp. 212-215.
Zelle, R. E. et al., "A systematic degradation of Zincophorin: a stereoselective synthesis of the $C_{17}$-$C_{25}$ fragment," J. Org. Chem., 1986, vol. 51, pp. 5032-5036.

* cited by examiner

*Primary Examiner*—Rebecca L Anderson
*Assistant Examiner*—Shawquia Young
(74) *Attorney, Agent, or Firm*—Connolly Bove Lodge & Hutz LLP

(57) ABSTRACT

A process for preparing optically active 2-methylalkan-1-ol of the general formula (III) comprising the following steps:
(i) carbonyl-selective reduction of 2-methylalk-2-en-1-al of the general formula (I) to 2-methylalk-2-en-1-ol of the general formula (II),
(ii) enantioselective hydrogenation of 2-methylalk-2-en-1-ol to the general formula (iii),
(iii) increasing the optical yield of the optically active 2-methylalkan-1-ol (III) obtained in step (ii) by a lipase-catalyzed acylation reaction,

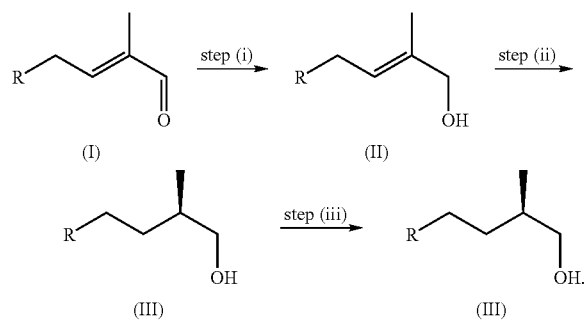

where the radical R means $C_1$-$C_{10}$-alkyl.

9 Claims, No Drawings

METHOD FOR PRODUCING AN OPTICALLY ACTIVE 2-METHYL-ALKANE-1-OL FROM THE CORRESPONDING 2-METHYLALK-2-EN-1-AL, COMPRISING CARBONYL-SELECTIVE REDUCTION, ENANTIOSELECTIVE HYDRATION AND LIPASE-CATALYZED, STEREOSELECTIVE ACYLATION IN ORDER TO ENRICH THE DESIRED

RELATED APPLICATIONS

This application is a national stage application (under 35 U.S.C. §371) of PCT/EP2005/010240 filed Sep. 22, 2005, which claims the benefit of German application 10 2004 047 836.8 filed Sep. 29, 2004.

The present invention relates to a novel process for preparing optically active 2-methylalkan-1-ol starting from 2-alkylpent-2-enal.

PRIOR ART

The preparation of optically active 2-methylpentan-1-ol ("methylpentanol") by various processes has previously been described in the literature. Thus, for example, M. A. Jermyn et al. (*Aust. J. Chem.* 1967, 20, 2283-2284) obtain R-methylpentanol by hydrolyzing the p-toluenesulfonate of L-valine (R)-2-methylpentyl ester. Oppolzer et al. (*Helv. Chim. Acta* 1985, 68, 212-215) obtain R-methylpentanol by diastereoselective ester enolate alkylation of a chiral sultam. Danishefsky et al. (*J. Org. Chem.* 1986, 51, 5032-5036) obtain R-2-methylpentanol by diastereoselective imide enolate alkylation of a chiral oxazolidinone. Effenberger et al. (*Tetrahedron: Asymmetry* 1993, 4, 823-833) obtain R-methylpentanol from racemic methylpentanol by lipase-catalyzed enantioselective acylation. The processes described above produce optically active methylpentanol in an economically unsatisfactory way because of costly starting materials, multistage synthesis, insufficient yields or very elaborate purification.

STATEMENT OF OBJECT

It is therefore an object of the present invention to provide a process for preparing optically active 2-methylalkan-1-ol that avoids, completely or at least partly, the disadvantages described above.

DESCRIPTION OF THE INVENTION

We have found that this object is achieved by a process for preparing optically active 2-methylalkan-1-ol of the general formula (III) comprising the following steps:
(i) carbonyl-selective reduction of 2-methylalk-2-en-1-al of the general formula (I) to 2-methylalk-2-en-1-ol of the general formula (II),
(ii) enantioselective hydrogenation of 2-methylalk-2-en-1-ol to the general formula (iii),
(iii) increasing the optical yield of the optically active 2-methylalkan-1-ol (III) obtained in step (ii) by a lipase-catalyzed acylation reaction,

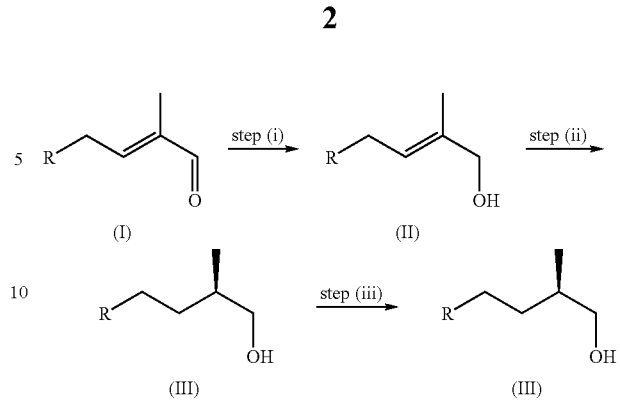

where the radical R means $C_1$-$C_{10}$-alkyl.

Only one enantiomer (III) is drawn in the formula scheme shown above. However, it is pointed out that the process of the invention also includes the preparation of the respective other enantiomer (III)—which is not drawn herein. The enantiomer (III) which is desired in each case can be obtained through selecting the appropriate catalyst system in step (ii).

In the formula images (I) to (III) shown above, the radical R means $C_1$-$C_{10}$-alkyl, where the alkyl radical may be straight-chain or branched, in particular methyl, ethyl, n-propyl and isopropyl, n-butyl, isobutyl, tert-butyl, pentyl, hexyl, heptyl, octyl, nonyl and decyl. This definition also comprises in addition substituted alkyls in which one or more, preferably one to three, hydrogen atoms are replaced by radicals such as F, Cl, Br, I, $NO_2$, $NH_2$, NH(alkyl), $N(alkyl)_2$, OH, SH, CN.

The individual steps of the process are described below:

Step (i): Carbonyl-Selective Reduction

The carbonyl-selective reduction of 2-methylalk-2-en-1-al to 2-methylalk-2-en-1-ol can be carried out by various processes known to the skilled worker. Examples of such processes comprise hydride-transferring reagents or catalysts such as, for example, main group element hydrides or transition metal complexes which can act as catalysts, transfer hydrogenations, reductions with metals or low valency metal salts, diimine reductions or hydrogenations. A compilation of such processes is described for example in R. L. Larock, *Comprehensive Organic Transformations*, Wiley-VCH, New York, 1999.

Depending on the selectivity of the catalyst system used in step (i) and on the chosen conditions, small amounts of the over-hydrogenated product (III) may be produced as racemate in step (i). Since this racemate (III) could impair the optical yield of the enantioselective double-bond hydrogenation provided in step (ii), it is advisable, following step (i), if appropriate to carry out a purification of the 2-methylalk-2-en-1-ol (II) produced, in order to remove any unreacted starting material (I) or over-hydrogenated racemic (III).

Such a purification can preferably take place by distillation, and it may be appropriate in particular for increasing the yield to add a higher-boiling component to the reaction mixture to be separated.

Step (ii): Enantioselective Hydrogenation

The enantioselective hydrogenation of 2-methylalk-2-en-1-ol to optically active 2-methylalkan-1-ol can be carried out using transition metal complex catalysts, in particular those with transition metals of groups 8-11.

Transition metal complex catalysts can be formed from a metal-containing precatalyst and a ligand.

Complexes comprising Ru, Rh, Ir, Pd, Pt are preferred as precatalyst, and complexes comprising Ru and Rh are particularly preferred as precatalyst.

Such preferred precatalysts are metal complexes for example $RhCl_3$, $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$, $Rh_6(CO)_{16}$ and $RuCl_3$, $Ru(acac)_3$, $[Ru(benzene)Cl]_2$, $[Ru(cymene)I_2]$, $Ru(methallyl)_2(cod)$.

The transition metal compounds and complexes mentioned, and further suitable ones, are known and described in the literature or can be prepared by the skilled worker in analogy to the compounds already known.

Ligands are P, As, Sb-containing compounds as well as compounds which are linked via a carbon atom to the transition metal catalyst complex fragment.

Chiral P-containing ligands are particularly preferred.

Particularly preferred ligands are phosphorus-containing compounds with the ability to develop atropisomerism in relation to two aryl or hetaryl systems as depicted below:

where the radicals have the following meaning:

R1, R2 (identical or different): subst. or unsubst. aryl, heteroaryl, alkyl, cycloalkyl, where the subst. may be H, halogen, alkyl, alkoxy R3, R4 (identical or different): subst. or unsubst. aryl, heteroaryl, alkyl, cycloalkyl, where the subst. may be H, halogen, alkyl, alkoxy R5, R5', R6, R6' (identical or different): with R=H, halogen, alkyl, aryl, alkoxy, amino, thio R7, R7' (identical or different): with R=H, halogen, alkyl, aryl, alkoxy, amino, thio or: R5, R5' (identical or different): with R=H, halogen, alkyl, aryl, alkoxy, amino, thio and R6 and R7, R6' and R7' form one or more rings which may comprise a further 1 or 2 double bonds (=fused aromatic ring) and/or may comprise heteroatoms (O, N, S)

R8, R8' (identical or different): with R=H, halogen, alkyl, aryl, alkoxy, amino, thio X, X' (identical or different): with X=S, O, NR9
  R9=H, alkyl, aryl, acyl, $SO_2R10$
  R10=aryl, alkyl, fluoroalkyl, $CF_3$ Particularly suitable ligands for the catalyst system used in step (ii) are the following ligands known from the literature:

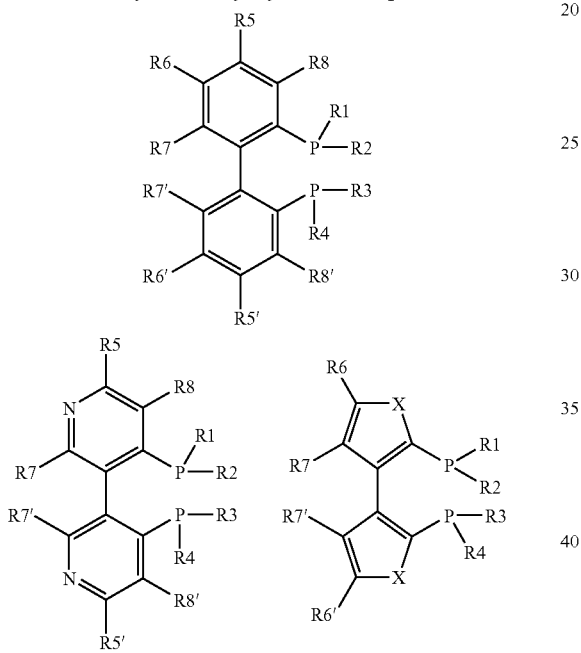

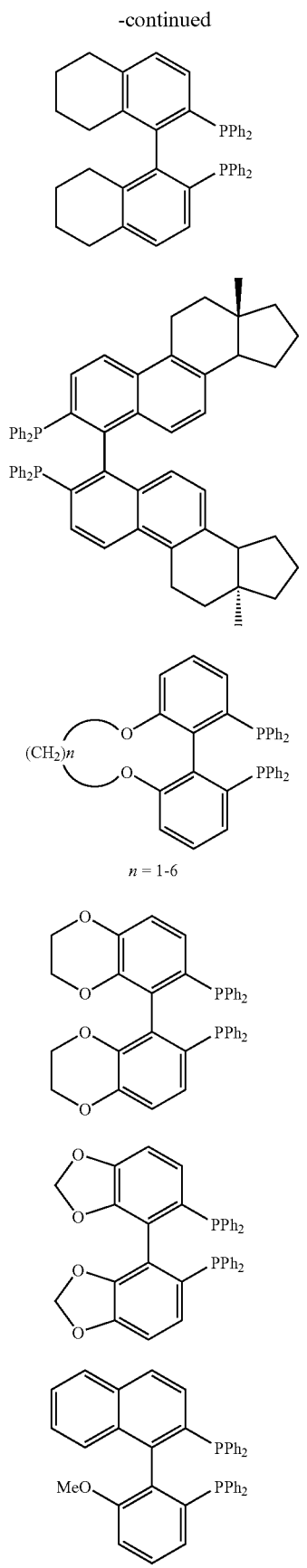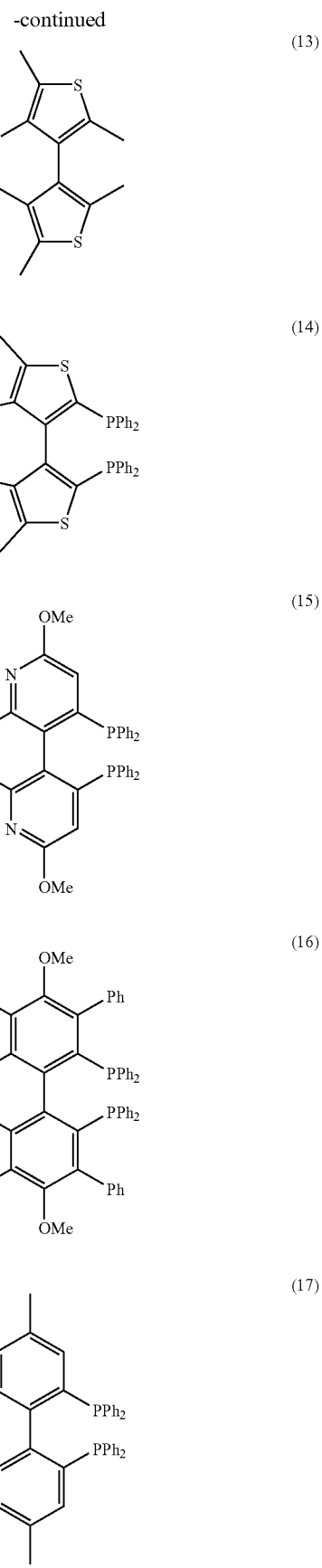

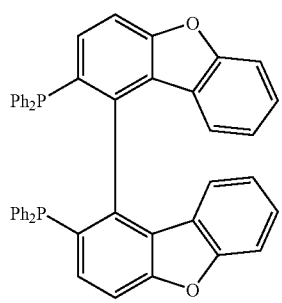
(18)
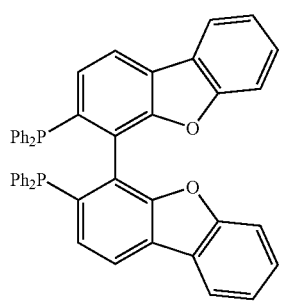
(19)
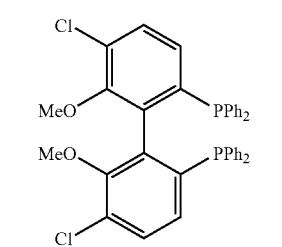
(20)
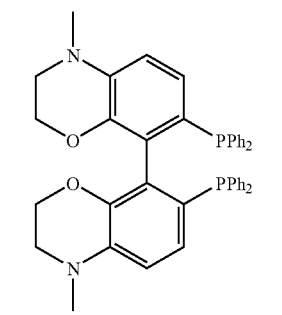
(21)
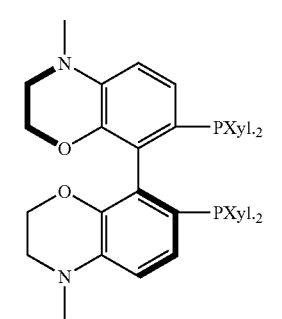
(22)
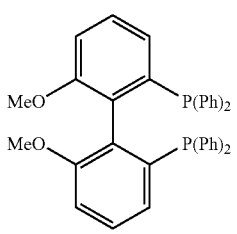
(23)
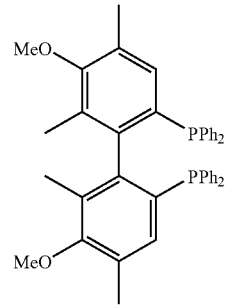
(24)
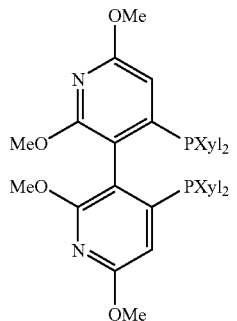
(25)
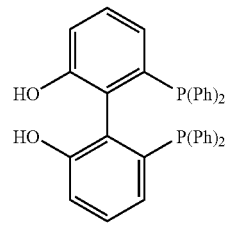
(26)
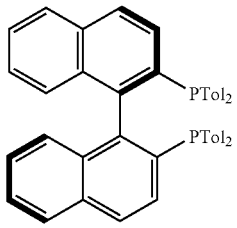
(27)
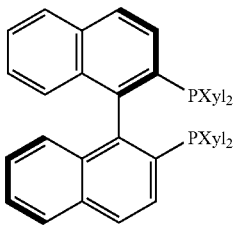
(28)

-continued

(29) 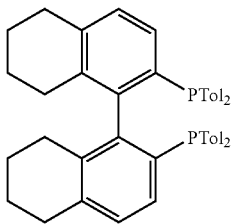

(30) 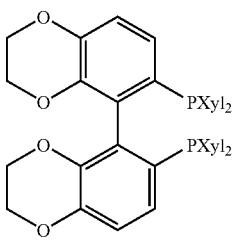

(31) 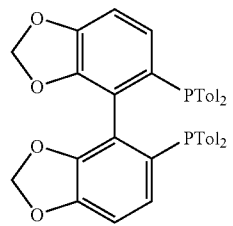

(32) 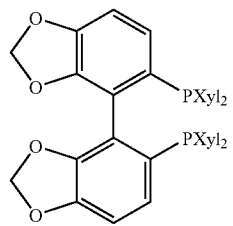

(33) 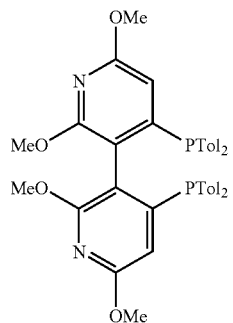

(34) 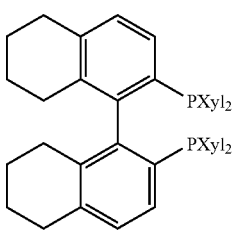

-continued

(35) 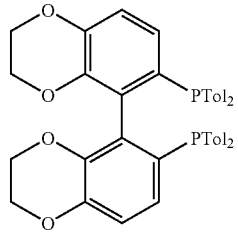

Preparation of the abovementioned transition metal complex catalysts from precatalyst and ligand is known and described in the literature, e.g. H. U. Blaser, B. Pugin, F. Spindler in "Applied homogeneous and heterogeneous catalysis with organometallic compounds", Ed. B. Cornils, W. A. Herrmann, p. 992 ff. VCH Weinehim, 1996, ISBN, 3-527-29286-1.

The reaction temperature for the enantioselective hydrogenation can be between −10° C. and 150° C., preferably between 0-120° C., particularly preferably between 10-100° C.

The reaction pressure for the enantioselective hydrogenation can be between 0.1 to 600 bar, preferably between 50 and 250 bar.

The catalyst used for step (ii) is normally employed in a cat:substrate ratio of <1:1000, preferably <1:5000.

The reaction time normally depends on the reaction temperature and on the pressure conditions prevailing during the reaction and the amounts of catalyst used; it is normally between 1 and 50 hours, preferably 5 to 25 hours.

The following solvents can preferably be used: methanol, ethanol, i-propanol, propanol, butanol, sec-butanol, tert-butanol, $CH_2Cl_2$, $CHCl_3$, dichloroethane, EtOAc, THF, TBME, $Et_2O$, $Bu_2O$, toluene, xylene, benzene, alkanes of the general formula $C_nH_{2n+2}$ with n=5-15 and mixtures thereof.

Methanol, ethanol, propanol, i-propanol are particularly preferred.

Step (iii): Increasing the Optical Yield of the Optically Active 2-Methylalkan-1-ol (III) Obtained in Step (ii) by a Lipase-Catalyzed Acylation Reaction.

Step (iii) serves to improve even further the ratio obtained in step (ii) of the optical isomers of the 2-methylalkan-1-ol (III). For this purpose, the mixture obtained in step (ii) is reacted (acylated) with an acylating agent under the catalytic action of a lipase, with the lipase selectively acylating one enantiomer (III) and leaving the other enantiomer (III) unchanged.

The lipase preferably acylates the enantiomer (III) which was not formed in enantiomeric excess in step (ii) and thus leaves the product (III) formed in enantiomeric excess in step (ii) unchanged by lipase. The fact that the enantiomer not formed in excess in step (ii) is completely reacted by acylation leads to an increase in the optical purity—defined as enantiomeric excess—of the enantiomer (III) formed in enantiomeric excess in step (ii).

The acylation product of (III) can be removed from the nonacylated enantiomer (III) by conventional processes such as chromatography, distillation or extraction.

The lipases employed in step (iii) may be derived from a large number of organisms, for example mammals (pig), but especially from microorganisms. Preferred lipases are those derived from the species *Pseudomonas* or *Burkholderia* or have been modified, starting therefrom, by genetic manipulation processes, particularly preferably from *Burkholderia plantarii* or *Pseudomonas fluorescens*.

The following lipases are particularly preferably used in step (iii): PFL Fluka (from Pseudomonal fluorescens), Novo 435 (Novozymes), Amano PS-C1, Amano PS-C2 and Amano PS-D1 (from *Burkholderia cepacia*, CAS No. 9001-62-1).

The lipases can be employed in dissolved form or else in carrier-bound form. A carrier-bound lipase is preferably used.

Acylating agents which can be employed for step (iii) are a large number of carboxyl derivatives which selectively acylate the substrate (III) under lipase catalysis. Preferred acylating agents are acid anhydrides and alkenyl esters.

Cyclic acid anhydrides such as succinic anhydride or vinyl esters are particularly preferred.

Step (iii) can be carried out with or without additional solvent.

If a solvent is to be employed, the following solvents are preferred: $CH_3CN$, DMSO, NMP, $CH_2Cl_2$, $CHCl_3$, dichloroethane, EtOAc, THF, TBME, $Et_2O$, $Bu_2O$, 1,4-dioxane, acetone, 2-butanone, toluene, xylene, benzene, alkanes of the general formula $C_nH_{2n+2}$ with n=5-15 and mixtures thereof.

The preferred temperature for this step is between 0-60° C., particularly preferably between 5-35° C.

The reaction time may be, depending on the chosen conditions, between one hour and several days. Normally, the progress of the reaction in step (iii) is followed, and the reaction is stopped when the desired enantiomeric excess is reached.

The acylation product formed from one enantiomer (III) is then separated from the other, unreacted enantiomer (III). If an acid anhydride has been employed as acylating agent, the removal of the acylated product can preferably take place by extraction with aqueous base solution.

The process of the invention can be carried out either discontinuously or continuously in all steps; however, it is also possible to carry out individual steps such as, for example, step (ii) continuously, and the other steps discontinuously.

Experimental Section

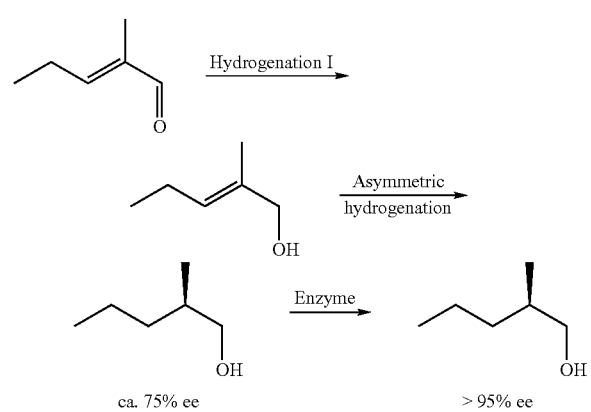

EXAMPLE 1

Preparation of 2-methylpent-2-en-1-ol using $LiAlH_4$ 595 mmol (58.4 g) of 2-methylpent-2-enal in 250 ml of diethyl ether are added dropwise to a suspension of 745 mmol (28.28 g) of lithium aluminum hydride in 550 ml of diethyl ether at −78° C. The mixture is stirred at 0° C. for 30 min and at room temperature for 1.5 h and again cooled to 0° C., and 50 ml of water are added dropwise over the course of 40 min. After the addition is complete, 30 ml of a 13% strength sodium hydroxide solution and then a further 25 ml of water are added dropwise. The resulting colorless suspension is filtered through Celite filter gel, dried over $MgSO_4$ and concentrated in a rotary evaporator under atmospheric pressure. The crude product is distilled at 52° C. and 11 mbar. 467 mmol (46.8 g, 79% yield) of 2-methylpent-2-en-1-ol are obtained.

GC: detector: FID; separating column: 25 m*0.32 mm OV-1 (Macherey & Nagel); film thickness=0.5 μm; temperature programme: 50° C., 2', 20° C./', 300° C.: RT=7.99 min 2-methylpent-2-en-1-ol.

EXAMPLE 2

Preparation of 2-methylpent-2-en-1-ol using Ru/Fe/C cat

A mixture of 349 mmol (35.0 g) of 2-methylpent-2-en-1-al, 17 ml of MeOH, 1.5 g of $NMe_3$ and 0.35 g of BV 191 pass. is stirred at 60° C. under a pressure of 40 bar of hydrogen for 22 h. Cooling to room temperature and filtration result in a crude product with the following composition (GC area %; without MeOH and $NMe_3$):

GC: detector: FID; separating column 30 m×0.32 mm Optima wax (Macherey & Nagel); film thickness=0.5 μm; temperature programme: 50° C., 2', 20° C./', 150° C., 15', 20° C./', 300° C.;

| RT | Area % | Compound |
| --- | --- | --- |
| 3.91 | 3.57 | 2-Methylpentanal |
| 4.21 | 0.34 | 2-Propylacrolein |
| 5.60 | 6.96 | 2-Methylpent-2-enal |
| 6.80 | 22.61 | 2-Methylpentanol |
| 7.59 | 63.4 | 2-Methylpent-2-en-1-ol |

EXAMPLE 3

Hydrogenation of 2-methylpent-2-en-1-ol with Ru/Josiphos System

13 μmol (7.7 mg) of Josiphos and 26 μmol (2.5 mg) of methanesulfonic acid are successively added to a suspension of 13 μmol (4.2 mg) of $Ru(COD)(methallyl)_2$ in 10 ml of MeOH, and the mixture is stirred in a glove box at room temperature for 30 min. The resulting solution is added to a solution of 65 mmol (6.51 g) of 2-methylpent-2-en-1-ol in 30 ml of MeOH in an autoclave under protective gas. The mixture is stirred at 25° C. under a pressure of 85 bar of hydrogen for 17 h. The crude product has the composition detailed below (GC area % without MeOH) and an ee of 58%.

GC: detector: FID; separating column 30 m×0.32 mm Optima wax (Macherey & Nagel); film thickness=0.5 μm; temperature programme: 50° C., 2', 20° C./', 150° C., 15', 20° C./', 300° C.;

| RT | Area % | Compound |
| --- | --- | --- |
| 5.17 | 1.86 | 1,1'-Dimethoxy-2-methylpentane |
| 7.12 | 97.82 | 2-Methylpentanol |
| 7.9 | 0.08 | 2-Methylpent-2-en-1-ol |

GC separation of R-, S-2-methylpentanol (4 blank samples necessary): column switching with precolumn: 10 m*0.25 mm Optimal (Macherey & Nagel) FD=0.5 microm, and chiral column: 30 m*0.25 mm BGB174 (BGB-Analytikvertrieb) FD=0.25 microm; oven temp.: 60° C. isothermal; precolumn: 0.3 bar He, chiral column: 1.1 bar He; column switching: RT=2.9 to 3.5; valve 1=On; RT=2.9 min: increase in the precolumn pressure to 1.3 bar for 0.3 min: RT of R-2-methylpentanol=1.9 min; RT of S-2-methylpentanol=4.1 min.

EXAMPLE 4

Hydrogenation of 2-methylpent-2-en-1-ol Using Ru/Solphos System

13 μmol (8.6 mg) of R-Solphos and 26 μmol (2.5 mg) of methane sulfonic acid are successively added to a suspension of 13 μmol (4.2 mg) of Ru(COD)(methallyl)$_2$ in 10 ml of MeOH, and the mixture is stirred in a glove box at room temperature for 30 min. The resulting solution is added to a solution of 260 mmol (26.04 g) of 2-methylpent-2-en-1-ol in 120 ml of MeOH in an autoclave under protective gas. The autoclave is closed and, after injection of 280 bar of nitrogen, put in the intended location. It is stirred at 40° C. under a pressure of 200 bar of hydrogen for 17 h. The crude product has the composition detailed below (GC area % without MeOH) and an ee of 74%

| RT | Area % | Compound |
|---|---|---|
| 4.63 | 1.66 | 1,1'-Dimethoxy-2-methylpentane |
| 6.52 | 79.87 | 2-Methylpentanol |
| 7.29 | 17.92 | 2-Methylpent-2-en-1-ol |

EXAMPLE 5

Lipase-Catalyzed Acylation 50 g (490 mmol) of R-2-methylpentanol with 66% ee were introduced into 500 ml of MTBE at RT, and 24.5 g (245 mmol) of succinic anhydride and 2.5 g of Amanolipase PS-D on clay were added and stirred at RT for 2 d. The progress of the reaction was followed by GC. As soon as the target ee is reached, the enzyme is filtered off and the filtrate is washed twice with 500 g of 10% sodium carbonate solution each time. The combined aqueous phases were then back-extracted once with 250 ml of MTBE; the combined organic phases were dried over MgSO$_4$ and freed of MTBE, and the residue was fractionally distilled.

14.5 g (35% of theory) of R-2-methylpentanol with 97% ee and >98% chem. purity were obtained as a colorless oil.

EXAMPLE 6

Lipase-Catalyzed Acylation 50 g (490 mmol) of R-2-methylpentanol with 66% ee were introduced into 200 ml THF at RT, and 24.5 g (245 mmol) of succinic anhydride and 0.5 g of Amanolipase PS-D on clay were added and stirred at RT for 2 h. The progress of the reaction was followed by GC. As soon as the target ee is reached, the enzyme is filtered off and the filtrate is, after addition of 100 ml of MTBE, washed twice with 500 g of 10% sodium carbonate solution each time. The combined aqueous phases were then back-extracted once with 250 ml of MTBE; the combined organic phases were dried over MgSO$_4$ and freed of MTBE, and the residue was fractionally distilled.

25.1 g of R-2-methylpentanol with 97% ee and >98% chem. purity were obtained as a colorless oil.

We claim:

1. A process for preparing optically active 2-methylalkan-1-ol of the general formula (III)

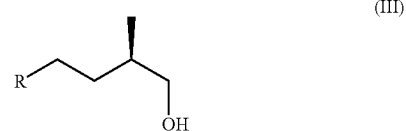

comprising the steps of:
(i) carbonyl-selectively reducing 2-methylalk-2-en-1-al of the general formula (I)

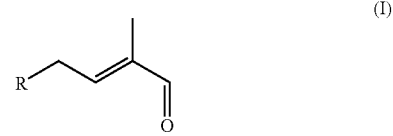

to 2-methylalk-2-en-1-ol of the general formula (II)

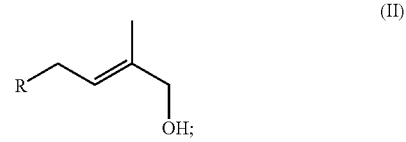

(ii) enantioselectively hydrogenating the 2-methylalk-2-en-1-ol of the general formula (II) to the optically active 2-methylalkan-1-ol of the general formula (III) in the presence of a transition metal complex catalyst comprising a phosphorus-containing chiral compound of formula (IV) as a ligand

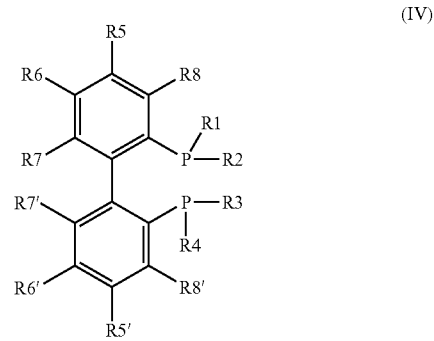

wherein
R1, R2, R3, and R4, identically or differently, are substituted or unsubstituted aryl, heteroaryl, alkyl, or cycloalkyl; and
R5, R5', R6, R6', R7, R7', R8, and R8', identically or differently, are H, halogen, alkyl, aryl, alkoxy, amino, or thio; and wherein said phosphorus-containing chiral compound of formula (IV) possesses the ability to develop atropisomerism in relation to two aryl or hetaryl systems;

(iii) increasing the optical yield of the optically active 2-methylalkan-1-ol (III) obtained in step (ii) by subjecting it to a lipase-catalyzed acylation reaction;

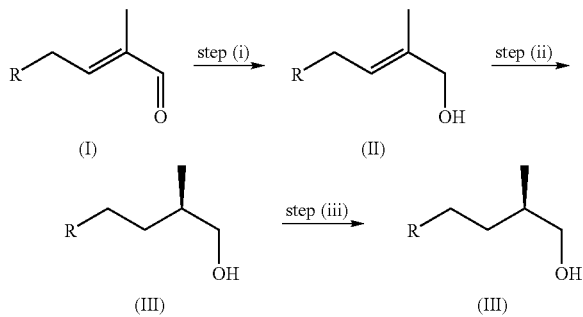

wherein R is $C_1$ to $C_{10}$ alkyl.

2. The process according to claim 1, wherein R is methyl.

3. The process according to claim 1, wherein step (i) is carried out using a heterogeneous hydrogenation catalyst.

4. The process according to claim 1, wherein the transition metal of said transition metal complex catalyst is Ru, Rh, Ir, Pd, or Pt.

5. The process according to claim 1, wherein said transition metal complex catalyst comprises a ligand selected from the group consisting of (R)-2,2'-bis-diphenylphosphanyl-[1,1'] binaphthalenyl; (S)-2,2'-bis-diphenylphosphanyl-[1,1]bi-naphthalenyl; (R)-6,6'-bis-diphenylphosphanyl-2,3,2',3'-tetrahydro-[5,5']bi[benzo[1,4]dioxinyl]; (S)-6,6'-bis-diphenylphosphanyl-2,3,2',3'-tetrahydro-[5,5']bi[benzo[1,4]dioxinyl]; (R)-7,7'-bis-diphenylphosphanyl-4,4'-dimethyl-3,4,3',4'-tetrahydro-2H,2'H-8,8']bi[benzo[1,4]oxazinyl]; and (S)-7,7'-bis-diphenylphosphanyl-4,4'-dimethyl-3,4,3',4'-tetrahydro-2H,2'H-[8,8']bi[benzo[1,4]oxazinyl].

6. The process according to claim 1, wherein step (iii) is carried out using Amano lipase PS-D1 (CAS No. 9001-62-1), PS-C1 or PS-C2 as a lipase.

7. The process according to claim 1, wherein step (iii) is carried out using succinic anhydride as an acylating agent.

8. The process according to claim 1, wherein step (iii) is carried out in the presence of a solvent selected from the group consisting of THF, MTBE, diethyl ether, toluene, 1,4-dioxane, and mixtures thereof.

9. The process according to claim 1, further comprising a distillation step to purify the 2-methylalk-2-en-1-ol (II) obtained in step (i) and which is carried out after step (i) but before step (ii).

* * * * *